US009820898B2

(12) United States Patent
Welch

(10) Patent No.: US 9,820,898 B2
(45) Date of Patent: Nov. 21, 2017

(54) BANDAGE PULLING TOOL AND USE OF SAME TO PREPARE AND WRAP BANDAGES

(75) Inventor: Jo Ann Welch, Cranbrook (CA)

(73) Assignee: Jo Ann Welch, Cranbrook (CA)

( * ) Notice: Subject to any disclaimer, the term of this patent is extended or adjusted under 35 U.S.C. 154(b) by 633 days.

(21) Appl. No.: 12/777,642

(22) Filed: May 11, 2010

(65) Prior Publication Data

US 2011/0282258 A1  Nov. 17, 2011

(51) Int. Cl.
*A61F 13/00* (2006.01)
*A61F 15/00* (2006.01)

(52) U.S. Cl.
CPC .................. *A61F 15/005* (2013.01)

(58) Field of Classification Search
USPC ........... 602/42, 3; 5/81.1 R, 81.1 HS, 81.1 T, 5/625; 128/851, 877; 2/323; 280/87.042, 304.1; D8/14
See application file for complete search history.

(56) References Cited

U.S. PATENT DOCUMENTS

| | | | | |
|---|---|---|---|---|
| 2,559,160 A | * | 7/1951 | Jacob | 254/134.3 FT |
| 2,641,760 A | * | 6/1953 | Syracuse | 2/460 |
| 3,754,486 A | * | 8/1973 | Mariner | 81/63 |
| 4,012,799 A | * | 3/1977 | Rutherford | 5/81.1 R |
| 4,989,846 A | * | 2/1991 | Quinn | 269/54.5 |
| 5,501,441 A | * | 3/1996 | Kegley | 269/289 R |
| D387,254 S | * | 12/1997 | Klamm | D8/14 |
| 6,694,779 B1 | * | 2/2004 | Dreger | 63/33 |
| D626,391 S | * | 11/2010 | Vigil | D8/14 |
| 2002/0158437 A1 | * | 10/2002 | Carbonero | 280/87.041 |
| 2008/0042387 A1 | * | 2/2008 | Lesko | 280/87.042 |

FOREIGN PATENT DOCUMENTS

GB  2424828 A  * 10/2006  ............... A61G 7/10

OTHER PUBLICATIONS

Read, Samantha; Top 10 Fashion Trends of the 80's; Hilary Magazine;pp. 2-3; www.hilary.com/fashion/quickie-80sfashion.html.*
"T-shirt clip"; www.ebay.com.*
Wikipedia article—"triangular bandage"; p. 2 of 3; http://en.wikipedia.org/wiki/Bandage.*
"Deluxe Oak Hardwood Transfer Board"; www.allegromedical.com; Oct. 20, 2007.*

* cited by examiner

*Primary Examiner* — Ophelia A Hawthorne
*Assistant Examiner* — Caitlin Carreiro
(74) *Attorney, Agent, or Firm* — Kyle R. Satterthwaite; Ryan Dupuis; Ade & Company, Inc.

(57) ABSTRACT

A bandage pulling tool has a thin elongate body and a hole extending transverse to a longitudinal axis of the thin elongate body proximate an end thereof. In use, a first end of a bandage is secured to the tool using the hole by passing a first end of the bandage through the hole for use as an anchor point to the tool. With the bandage thus secured to the tool in a position passing through the hole therein, the first end of the bandage can be passed from a first side of a body portion of an injured party to another behind the body portion using the elongated shape of the tool. Accordingly, a wrap around bandage can be applied to the patient with minimal, if any, movement of potentially injured areas compared to prior art techniques of manually feeding the bandage behind the injured party.

13 Claims, 5 Drawing Sheets

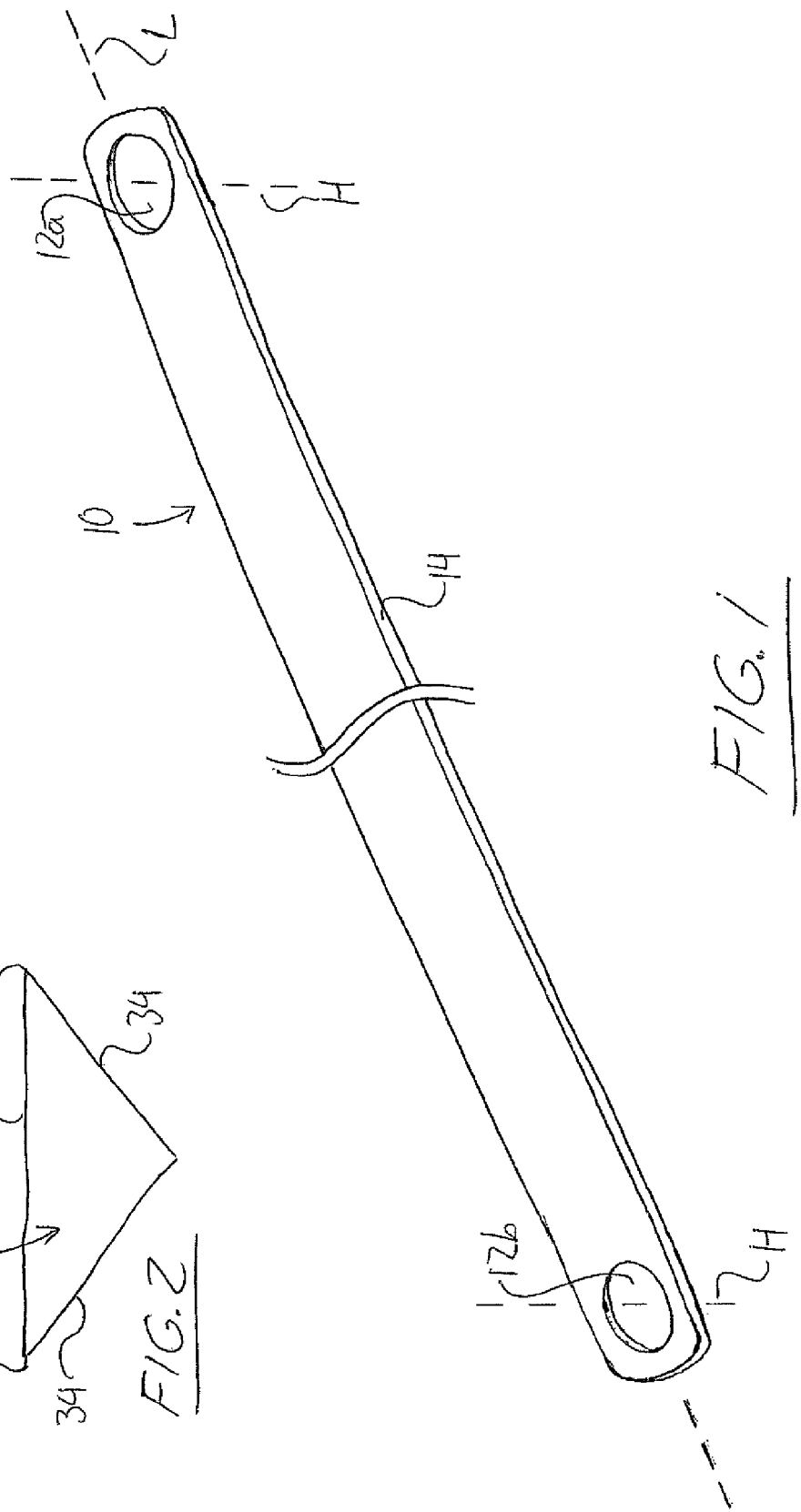

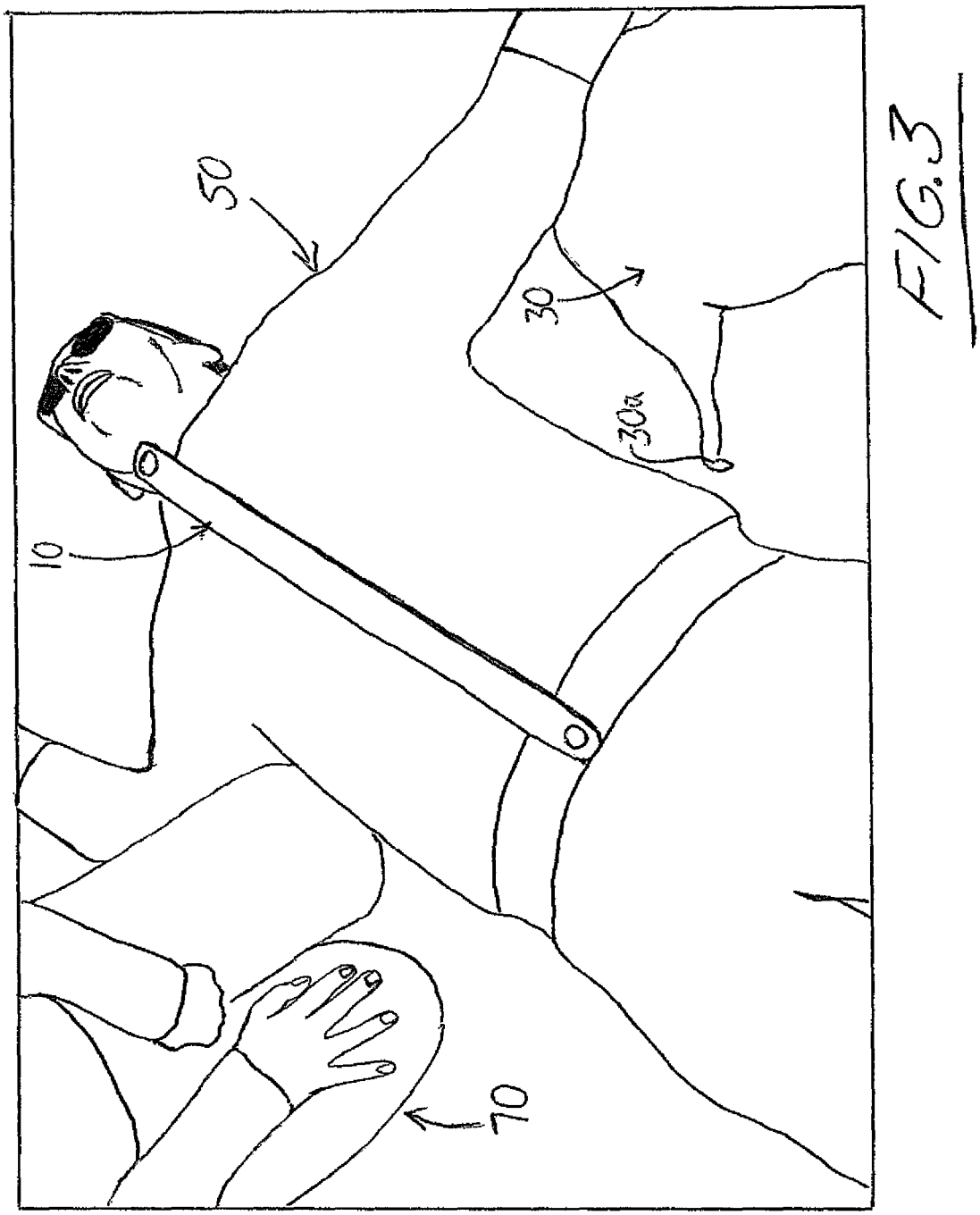

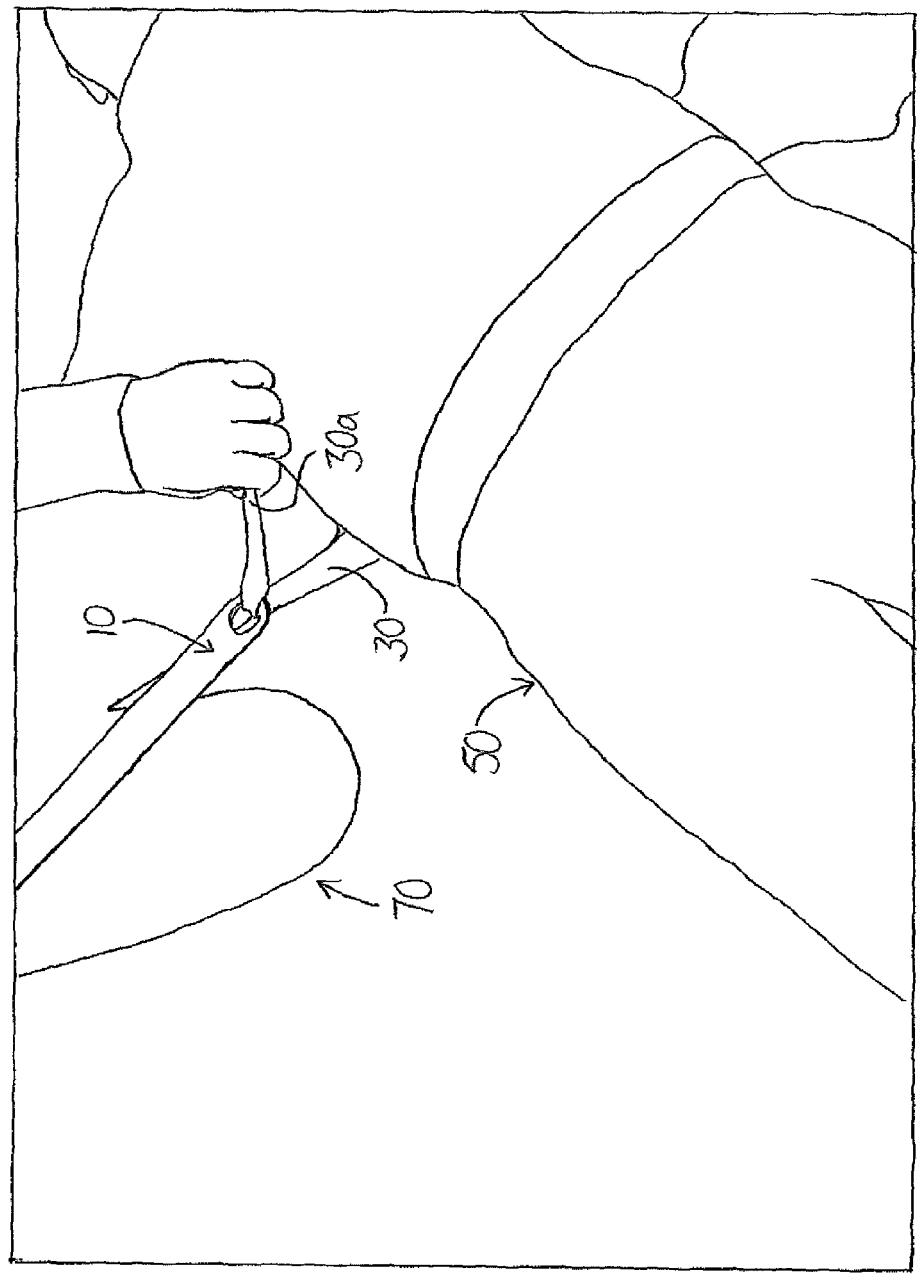

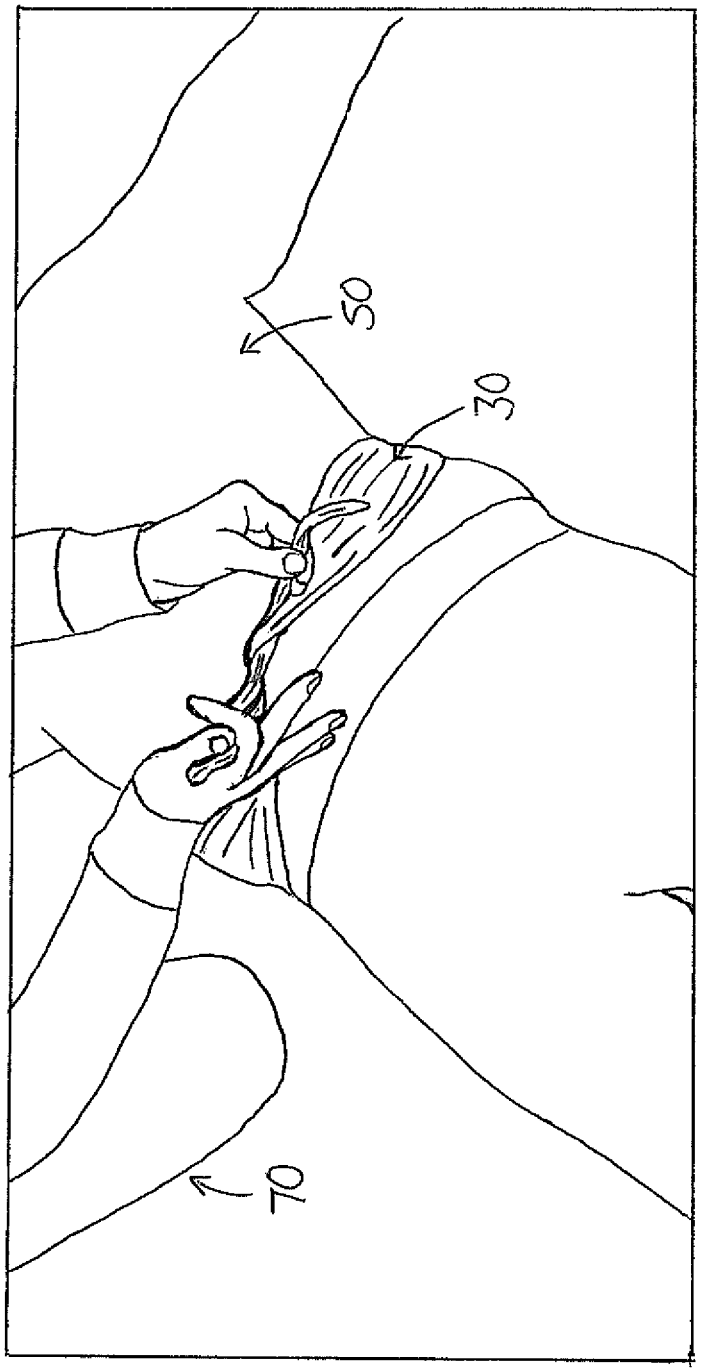

BANDAGE PULLING TOOL AND USE OF SAME TO PREPARE AND WRAP BANDAGES

FIELD OF THE INVENTION

The present invention relates generally to wrap around bandages for medical purposes, and more particularly to a tool for aiding in application of such bandages in such a way as to minimize or eliminate the need for movement of the injured party during such application.

BACKGROUND OF THE INVENTION

First responders arriving on the scene of an accident are relied upon to assess the medical condition of the injured party and may need to evacuate patients as efficiently and with the least patient discomfort as possible. Time can be of the essence, especially when serving at remote locations and/or in adverse conditions.

One difficulty sometimes faced in providing efficient treatment to an injured party on site is the application of bandage wrapping to an injured part of the body. For example, an accident victim lying on the ground may require a bandage to be wrapped around his or her torso or other body part. Conventional techniques for carrying out this task rely entirely on manual manipulation of the bandage, meaning that the responder must manually pass the bandage beneath the patients inured body part between that part and the ground surface behind it. In order to accommodate the respondents' hand, the body part must typically be lifted or otherwise manipulated to create the necessary space between the injured and the surface on which they lie. This movement of the patient may require significant physical effort by the responder, may cause significant discomfort to the patient, may risk aggravation of the patient's injury or injuries, and may be time inefficient if the responder is alone and struggling to simultaneously elevate the body part to be wrapped, manually feed one end of the bandage behind the patient from one side to the other and manually locate and retrieve the bandage from the other side of the patient once sufficiently fed behind him or her.

Accordingly, Applicant has recognized a need for new developments useful in addressing at least of these shortcomings of the prior art bandage wrapping techniques.

SUMMARY OF THE INVENTION

According to a first aspect of the invention there is provided a bandage pulling tool for aiding in wrapping of a bandage around a body portion of an injured party, the tool comprising an thin elongate body having first and second opposing ends separated along a longitudinal axis thereof and a first open holed end feature defined proximate the first end of the elongate body, the first open holed end feature defining a first hole having a first hole axis transverse to the longitudinal axis, whereby an end of the bandage can be passed through the first hole along the first hole axis for temporary securing of the bandage to the tool to enable passing of the first end of the tool, and the end of the bandage secured thereto, behind the body portion of the injured party from one side thereof to another in order to position ends of the bandage on opposite sides of inured party for subsequent closing of the bandage around the body portion thereof.

The thin structure of the tool can be easily slipped behind or beneath the injured with minimal or no movement of the body part(s) in question, while its length means that the end of the tool passed behind the user is easy to visually or manually locate as it reaches the side opposite from which it was fed. A user can thus avoid potentially painful or harmful manual displacement of the body part to be wrapped, and save time by not having to perform such movement of the injured party and not needing to fumble with and fish around for the end of the bandage behind the body part in question.

Preferably there is provided a second open holed end feature defined proximate the second end of the elongate body to enable selective securing of the bandage to either of the first and second open holed end features.

Preferably the thin elongate body is a single unitary member and the first open holed feature is defined integrally.

Preferably the single unitary member closes fully around the first hole.

Preferably the first open holed end feature has oppositely facing surfaces separated by a thickness thereof and defining a width thereof, the first hole being a through hole passing through the tool from one of the oppositely facing surfaces to the other with the oppositely facing surfaces closing fully around the first hole axis.

Preferably the single unitary member comprises a strip having opposite facing surfaces separated by a thickness thereof and side edges separated by a width thereof, the first hole being a through hole passing through the thickness of the strip from one of the oppositely facing surfaces to the other and being situated entirely between the side edges of the strip.

Preferably the elongate body and the first open holed end feature comprise plastic.

Preferably the elongate body comprises sterilizable material.

Preferably a length of the elongate body measured along the longitudinal axis thereof is between 15 and 30 inches long, and may for example be between 20 and 25 inches in some embodiments.

For use, the tool is provided in combination with the bandage, and the bandage may be wider at a center thereof than at the end thereof, with the size of the hole being such that pulling of the end of the bandage therethrough will releasably secure the bandage to the tool by wedging the wider portion of the bandage into the hole.

According to a second aspect of the invention there is provided a method of preparing a bandage for wrapping around a body portion of an injured party, the method comprising securing the bandage to a tool having a thin elongate body, at least in part, by passing an end of the bandage through a hole in the tool extending transverse to the longitudinal axis of the thin elongate body proximate an end thereof, whereby the tool can subsequently be used to pass the end of the bandage from one side of a body portion of an injured party to another behind the body portion.

Securing the bandage to the tool may comprise wedging a portion of the bandage wider than the end thereof into the hole by continued pulling of the end of the bandage after initial passage thereof through the hole.

According to a third aspect of the invention a method of wrapping a bandage around a body portion of an injured party is disclosed, the method comprising:

securing the bandage to a tool having a thin elongate body and a hole extending transverse to a longitudinal axis of the thin elongate body proximate and end thereof, including passing a first end of the bandage through the hole;

with the bandage secured to the tool in a position passing through the hole therein on a first side of the body portion of the injured party, passing the first end of the bandage behind the body portion of the inured party from the first side of the body portion to an opposite second side thereof;

releasing the bandage from the tool; and fastening the bandage in place in a condition closing fully around the body portion.

Preferably passing the first end of the bandage behind the body portion is carried out without manually moving the body portion.

Preferably, passing the bandage behind the body portion is carried out without manually moving the injured party.

BRIEF DESCRIPTION OF THE DRAWINGS

In the accompanying drawings, which illustrate exemplary embodiments of the present invention:

FIG. 1 is a schematic perspective view of a bandage pulling tool of the present invention.

FIG. 2 is a plan view of a conventional triangular bandage that can be used with the tool of FIG. 1.

FIG. 3 is a schematic illustration of a medical responder having reached an injured party and preparing to use the tool of FIG. 1 to wrap a bandage around the torso thereof.

FIG. 5 is a schematic illustration of the medical responder having used the tool to pull the end of the bandage to an opposite second side of the injured party, leaving an opposite end of the bandage behind on the first side.

FIG. 6 is a schematic illustration of the bandage being tied around the torso of the injured party once the tool is removed after the step shown in FIG. 5.

DETAILED DESCRIPTION

Figure 4:
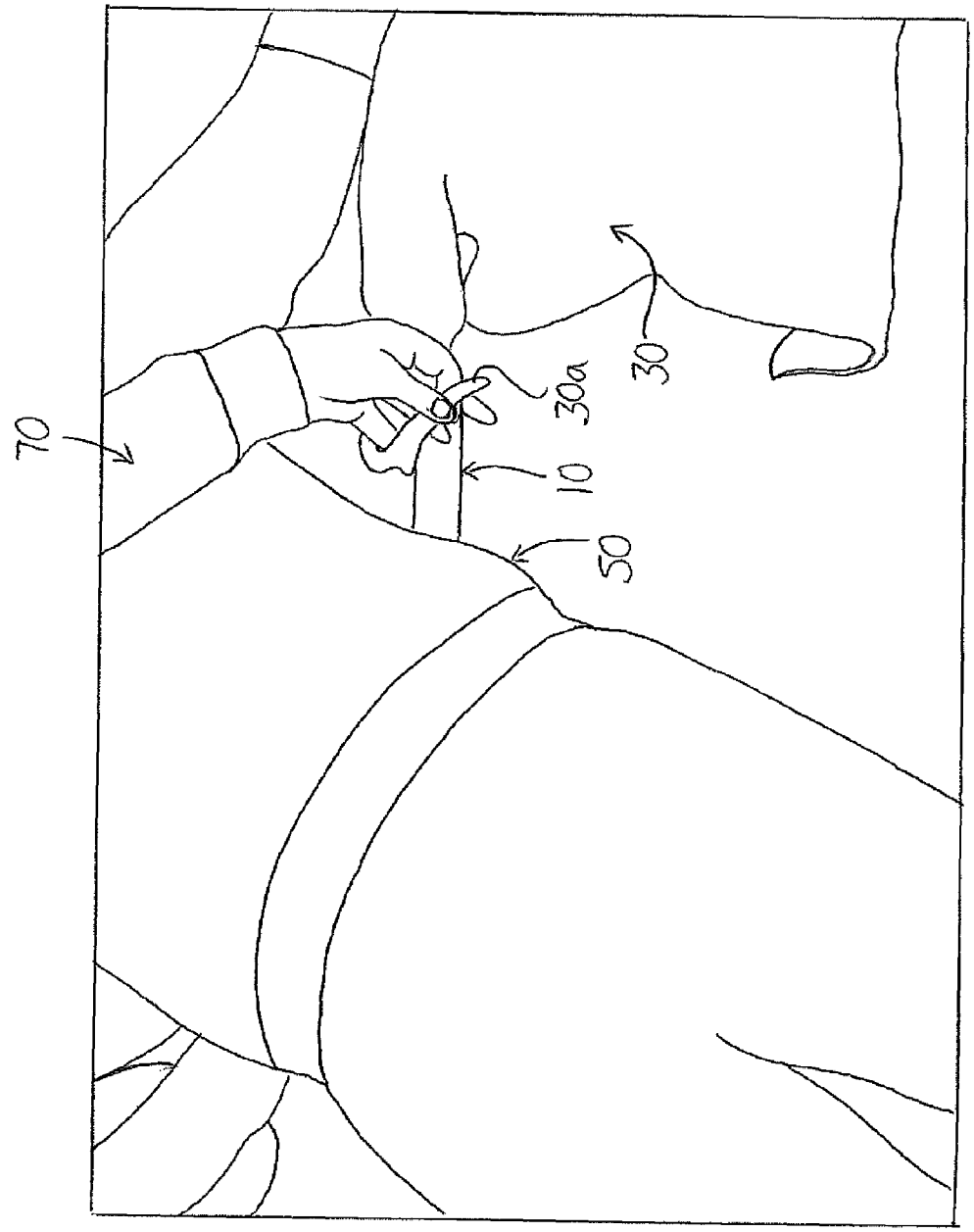
FIG. 4 is a schematic illustration of the medical responder securing an end of the bandage to the tool on a first side of the injured party.

FIG. 1 shows a tool 10 according to an embodiment of the present invention. The illustrated tool is a single, unitary body of integral plastic construction having a strip-like elongated shape. The tool has a length sufficient to span fully across the torso of an average human being, but has a substantially smaller width many times less than its length and an even smaller thickness many times less than its width. The tool has a substantially planar structure with flat, parallel top and bottom faces. Proximate each end of the tool 10, a circular through hole 12a, 12b passes perpendicularly through the top and bottom surfaces along a respective hole axis H perpendicular to a longitudinal axis L extending the length of the tool 10. Each circular through hole 12a, 12b is located between the side edges 14 defining the uniform thickness of the tool 10 without intersecting these side edges 14, and likewise is positioned entirely inward from the shorter end edges of the strip-like shape of the tool, leaving each circular through hole 12a, 12b continuously enclosed around its perimeter at the planar faces of the piece.

The open hole passing fully through the tool body adjacent each end provides an anchoring or fastening location at which bandage wrap can be secured thereto. FIG. 2, not drawn to scale with FIG. 1, schematically shows a triangular bandage 30 having three straight sides. The illustrated bandage 30 is isosceles in shape, having one longest side 32 longer than the remaining two equal sides 34. With the vertices at the opposite ends 30a, 30b of the longest side 32 considered to define opposing ends of the bandage, a selected one of the bandage ends 30a, 30b can be passed through either one of the circular through holes 12a, 12b of the tool 10. To secure the bandage 30 to the tool 10, the bandage can either be tied back onto itself via this passage through the circular through hole 12a, 12b in the tool, or with suitable sizing of the circular through hole 12a, 12b, pulling of the pointed end of the bandage sufficiently far through the circular through hole 12a, 12b will draw a gradually wider portion of the bandage 30 into the circular through hole 12a, 12b until the bunching or wedging of the bandage 30 against circumferential edge of the hole in the tool 10 is sufficient to frictionally retain the bandage in this wedged position secured to the tool.

With reference to FIGS. 3 to 6, use or operation of the tool in tending to an injured party believed to require a bandage wrap will now be described.

FIG. 3 schematically shows an injured person or patient 50 lying down on a horizontal floor or ground surface at an accident scene. An emergency medical responder 70 has arrived and is shown to have arrived with the combination of the tool 10 and triangular bandage 30 of FIGS. 1 and 2. To begin, the responder 70 has knelt down beside the patient 50 on one side of the patient's torso and has and placed the bandage 30 on the opposite side thereof. Moving to FIG. 4, in preparing to apply the bandage to the patient's torso, the responder has first gripped one end of the tool at the responder's side of the patient and has forced the opposite end of the tool across the patient's torso between the ground and the patient's back to the opposite side of the patient on which the bandage was initially placed. As shown, the responder now grasps the first end 30a of the bandage 30 and passes it through the circular through hole 12a at the end of the tool now on the same side of the patient as the bandage 30. The responder continues to the pull the triangular bandage 30 through the circular through hole 12a in the same direction until, sometime before the widest part of the bandage defined by the perpendicular line from the longest side 32 to the vertex or corner opposite thereof, the bandage wedges itself snugly within the circular through hole 12a.

The responder then draws the tool 10 entirely back to the side of the patient at which the responder is situated behind the patient, thereby drawing the first end 30a of the bandage to the same side of the patient as the responder with the tool's circular through hole 12a at which the first end of the bandage is secured. As shown in FIG. 5, the responder can now withdraw the first end 30a of the bandage from its wedged position in the circular through hole 12a to separate the tool and the bandage. The bandage now has its first end situated on the responder side of the patient, with its opposite second end remaining on the other side of the patient so that the bandage now fully passes behind the patient's torso from one side to the other. With the very thin tool being used to accomplish this transition of the one bandage end from one side to the other beneath the patient, no manual repositioning or shifting of the patient's torso or other body parts was required. As shown in FIG. 6, having easily fished the one bandage end out from behind the patient with the tool, the responder 70 can now tie or otherwise fasten the bandage to itself in front of the patient from thereover in the necessary position closing fully and snuggly around the patient's torso.

A prototype on which the drawings are based was made out of clear plastic, with a length of 20¼ (20.25) inches long, a width of 1⅛ (1.125) inches and a thickness of ⅛ (0.125) inches. The plastic material can be sterilized, as well as manufactured in safety colors and may have a degree of flexibility and resiliency to allow it to keep its default substantially linear shape while being able to fit into jump bags of varying sizes. The tool can be used by any emergency responders (first responders, emergency medical technicians or EMTs, paramedics, etc.) and also by other medically trained personnel (doctors, nurses, etc.) in hospitals, clinics or other medical facilities.

It will be appreciated that variations to the above tool structure, method of preparing the tool and bandage for use and method of using the tool to wrap the bandage may be made while remaining within the scope of the present invention. For example, while use of two bandage anchoring holes in the tool allows the responder to use either end and not have to worry about properly identifying which end is suitable for pulling a bandage, an alternate embodiment could instead feature a single hole. Furthermore, the strip-like structure of the tool body could be altered. For example, early prototypes were made by bending a wire coat hanger to form a linear elongate rod section with a looped end defining the bandage anchoring hole, and then wrapping the wire with medical tape. Although the above embodiments are described in terms of a triangular bandage, it will be appreciated that other shapes may similarly be used with the tool of the present invention. Even shapes that do not taper or are not sufficiently wide anywhere therealong to provide the friction fit wedging or bunching simply by pulling of the bandage end through the hole could still be used, for example relying on tying or other fastening of the fed-through bandage end back onto itself for the temporary releasable engagement to the tool. Although the example presented above for use of the tool involves wrapping of a bandage around the torso of the injured, it will be appreciated that the same tool may be used in bandaging of other portions of the body.

Since various modifications can be made in the invention as herein above described, and many apparently widely different embodiments of the same made within the spirit and scope of the claims without departing from such spirit and scope, it is intended that all matter contained in the accompanying specification shall be interpreted as illustrative only and not in a limiting sense.

The invention claimed is:

1. A bandage pulling tool for aiding in wrapping of a bandage around a body portion of an injured party, the tool comprising a resiliently flexible strip of material defining first and second opposing ends of the tool that are spaced apart along a longitudinal axis of the strip of material, the strip of material having a length that extends along the longitudinal axis, a width that is lesser than the length, a thickness that is lesser than the width, and a first hole passing through the thickness of the strip of material proximate the first end of the tool, whereby an end of the bandage can be passed through the first hole for temporary securing of the bandage to the tool to enable passing of the first end of the tool, and the end of the bandage secured thereto, behind the body portion of the injured party from one side thereof to another in order to position ends of the bandage on opposite sides of inured party for subsequent closing of the bandage around the body portion thereof.

2. The tool of claim 1 comprising a second hole passing through the thickness of the strip of material proximate the second end of the tool to enable selective securing of the bandage to the tool at either of the first and second holes.

3. The tool of claim 1 wherein the strip of material closes fully around the first hole.

4. The tool of claim 1 wherein the strip of material comprises plastic.

5. The tool of claim 1 wherein the strip of material comprises sterilizable material.

6. The tool of claim 1 wherein the length of the strip of material is between 15-inches and 30-inches.

7. The tool of any one of claims 1 to 6 in combination with the bandage, wherein the bandage is wider at a center portion thereof than at the end thereof and the size of each hole in the strip of material is such that pulling of the end of the bandage therethrough will releasably secure the bandage to the tool by wedging the center portion of the bandage into the hole.

8. A method of preparing a bandage for wrapping around a body portion of an injured party, the method comprising:
obtaining a tool having a resiliently flexible strip of material that defines first and second opposing ends of the tool that are spaced apart along a longitudinal axis of the strip of material, the strip of material having a length that extends along the longitudinal axis, a width that is lesser than the length, a thickness that is lesser than the width, and a first hole passing through the thickness of the strip of material proximate the first end of the tool;
securing the bandage to the tool, at least in part, by passing an end of the bandage through the first hole in the tool, whereby the tool can subsequently be used to pass the end of the bandage from one side of a body portion of an injured party to another behind the body portion.

9. The method of claim 8 wherein securing the bandage to the tool comprises wedging a portion of the bandage wider than the end thereof into the first hole by continued pulling of the end of the bandage after initial passage thereof through the first hole.

10. A method of wrapping a bandage around a body portion of an injured party, the method comprising:
obtaining a tool having a resiliently flexible strip of material that defines first and second opposing ends of the tool that are spaced apart along a longitudinal axis of the strip of material, the strip of material having a length that extends along the longitudinal axis, a width that is lesser than the length, a thickness that is lesser than the width, and a first hole passing through the thickness of the strip of material proximate the first end of the tool;
securing the bandage to the tool, including passing a first end of the bandage through the first hole;
with the bandage secured to the tool in a position passing through the first hole therein on a first side of the body portion of the injured party, passing the first end of the bandage behind the body portion of the inured party from the first side of the body portion of the injured party to an opposite second side thereof;
releasing the bandage from the tool; and
fastening the bandage in place in a condition closing fully around the body portion.

11. The method of claim 10 wherein securing the bandage to the tool comprises wedging a portion of the bandage wider than the end thereof into the first hole by continued pulling of the end of the bandage after initial passage thereof through the first hole.

12. The method of claim 10 wherein passing the first end of the bandage behind the body portion of the injured party is carried out without manually moving the body portion of the injured party.

13. The method of claim 10 wherein passing the first end of the bandage behind the body portion of the injured party is carried out without manually moving the injured party.

* * * * *